US00PP14809P2

(12) United States Plant Patent
Hanes

(10) Patent No.: US PP14,809 P2
(45) Date of Patent: May 25, 2004

(54) VERBENA PLANT NAMED 'LAN RED'

(50) Latin Name: *Verbena hybrida*
Varietal Denomination: Lan Red

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 98 days.

(21) Appl. No.: 10/389,096

(22) Filed: Mar. 13, 2003

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Susan B. McCormick
(74) *Attorney, Agent, or Firm*—Jondle & Associates, PC

(57) ABSTRACT

A verbena cultivar particularly distinguished by red colored flowers, vigorous growth and low trailing habit.

1 Drawing Sheet

Genus and species: Verbena hybrida.
Variety denomination: 'Lan Red'.

BACKGROUND OF THE NEW PLANT

The present invention comprises a new and distinct cultivar of verbena, botanically known as *Verbena hybrida*, and hereinafter referred to by the cultivar name 'Lan Red'. The new cultivar is asexually reproduced from vegetative cuttings and tissue culture resulting from the cross of the seed/pod parent 99-971-2, a scarlet orange proprietary line that is unnamed and unpatented ×'Tukana Scarlet' (U.S. Plant Pat. No. 12,578 Apr. 23, 2002), a dark red commercial line.

'Lan Red' is a product of a planned breeding program intended to create new verbena cultivars with red colored flowers, dark green foliage, vigorous growth and low trailing habit.

The new cultivar was created in 2000 in Gilroy, Calif. and has been asexually reproduced repeatedly by vegetative cuttings and tissue culture in Gilroy, Calif., Andijk, The Netherlands; Guatemala over a two year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Lan Red'. The data, which defines these characteristics, were collected from asexual reproductions carried out in Gilroy, Calif. The plant history was taken on 10 month old plants grown in one-gallon pots, in a double poly-greenhouse under natural light and color readings were taken in the greenhouse under natural lights. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Verbena hybrida.
*Commercial.*—Verbena.
Form: Low trailing annual, decumbent.
Growth and branching habit: Vigorous growing, moderate basal branching; low trailing habit.
Height: From soil level to top of blooms: Approximately 10–20 cm.
Width: Approximately 60–70 cm.
Time to produce a finished flowering plant: 11 weeks.
Outdoor plant performance: Typical bedding plant culture, full sun in the garden, hanging baskets or container plants.
Time to initiate and developed roots: Approximately 4–10 days in the greenhouse.
Root description: Fibrous, white.

THE LEAVES

Length: 3.7–5.0 cm.
Width: 1.3–2.9 cm.
Leaf blade shape: Ovate.
Leaf margin: Irregular, pinnatisect, crenately incised.
Apex aspect: Acute to Obtuse.
Base aspect: Acuminate.
Leaf color: Upper surface — close to RHS 137A (green); Underside — close to RHS 137B/C (green).
Texture: Pilose and a few glandular hairs.
Venation: Pinnate.
Venation color: RHS 145A (green).
Petiole length: 0.2–0.3 cm.
Petiole diameter: 0.15–2.0 cm.
Petiole color: RHS 145A (green).
Petiole texture: Pilose.

THE STEM

Length: 50–70 cm.
Diameter: 0.2 cm .
Internodes length: 4.0–6.5 cm.
Color: RHS 137B (green).
Texture: Pilose and a few glandular hairs.
Stem anthocyanin: No.

THE BUD

Shape: Linear.
Diameter: 0.25–0.3 cm.
Length: 1.1–1.5 cm.
Color at tight bud: RHS 45A (red).

THE FLOWER

Blooming habit: Flowers continuous throughout the growing season.
Inflorescence type: Spike.
Spike diameter: Approximately 4.0–6.5 cm.
Spike depth: Approximately 2.5–3.0 cm.
Peduncle length: 4.5–6.0 cm.
Peduncle diameter: 1.5 cm.
Peduncle color: RHS 137C (green).
Peduncle texture: Pilose; and short glandular hairs with violet hue.
Flower color: Upper petal surface is close to RHS 45B (red); Lower petal surface is RHS 47B (red).
Flower 'eye spot' color: RHS 160C (greyed-yellow).
Diameter: 0.25 cm.
Floret form: Salverform; sessile on spikes.
Floret (limb) diameter: Approximately 1.6–2.0 cm.
Corolla tube length: Approximately 2.0–2.7 cm.
Number florets per spike: 18–29.
Number of petals: Gamopetalous, five lobed.
Petal size: Length of one lobe — 0.9–1.0 cm; width of one lobe — 0.8–1.0 cm.
Petal lobe shape: Obcordate.
Petal apex shape: Deeply emarginated.
Petal base shape: Fused.
Petal margin: Entire.
Petal texture: Papillose.
Sepals: Five sepals whose margins are fused to each other along their length with a transparent membrane of less than 1 mm in width with one smaller sepal (7 mm) attached to the base of the calyx.
Calyx length: Approximately 1.1–1.2 cm.
Calyx width: Approximately 2.5 cm.
Calyx shape: Linear.
Calyx apex: Acute.
Calyx color: RHS 138A (green).
Lastingness of individual blooms: 6–8 days.
Fragrance: None.

THE REPRODUCTIVE ORGANS

Stamens: Anthers and filaments fused to upper half of corolla tube; four anthers with two pollen sacs per anther.
Pollen amount and color: Moderate, RHS 4C (yellow).
Pistil: One style approximately 1.6–1.8 cm.
Fruit seed set: Not observed.

DISEASE AND INSECT RESISTANCE

Tolerant to mildew.

COMPARISON WITH KNOWN CULTIVARS

'Lan Red' differs from its female parent 99-971-2 as follows: The female parent is a scarlet orange color with a darker leaf on a more upright plant. The 'Lan Red' is red on a moderately green leaf upright and spreading plant.

'Lan Red' differs from the male parent 'Tukana Red' as follows: The male parent has darker red color flowers and grows as a slightly more upright plant.

I claim:

1. A new and distinct cultivar of verbena plant as shown and described herein.

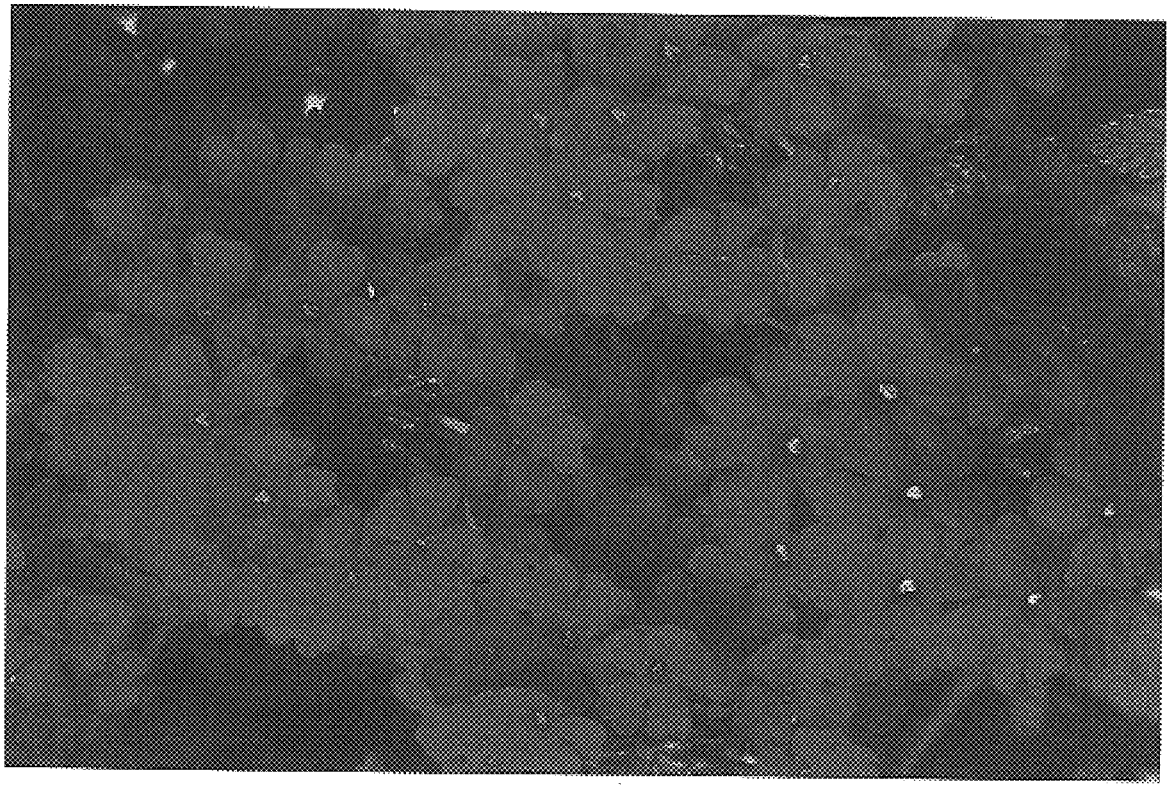

* * * * *